(12) United States Patent
Howell et al.

(10) Patent No.: US 10,029,227 B2
(45) Date of Patent: *Jul. 24, 2018

(54) OPTICAL SYSTEM FOR CHEMICAL AND/OR BIOCHEMICAL REACTIONS

(75) Inventors: James Richard Howell, Middlesbrough (GB); Benjamin Masterman Webster, Cleveland (GB); Mark Quentin Clark, Blackburn (GB); Richard Alfred Howell, Middlesbrough (GB)

(73) Assignee: IT-IS International Limited (GB)

(*) Notice: Subject to any disclaimer, the term of this patent is extended or adjusted under 35 U.S.C. 154(b) by 53 days.

This patent is subject to a terminal disclaimer.

(21) Appl. No.: 13/143,720

(22) PCT Filed: Jan. 8, 2010

(86) PCT No.: PCT/GB2010/000028
§ 371 (c)(1),
(2), (4) Date: Oct. 6, 2011

(87) PCT Pub. No.: WO2010/079338
PCT Pub. Date: Jul. 15, 2010

(65) Prior Publication Data
US 2012/0014835 A1    Jan. 19, 2012

Related U.S. Application Data

(60) Provisional application No. 61/143,391, filed on Jan. 8, 2009.

(51) Int. Cl.
*B01J 19/00* (2006.01)
*G01N 21/25* (2006.01)
*G01N 21/64* (2006.01)

(52) U.S. Cl.
CPC ........ *B01J 19/0046* (2013.01); *G01N 21/253* (2013.01); *G01N 21/6452* (2013.01);
(Continued)

(58) Field of Classification Search
None
See application file for complete search history.

(56) References Cited

U.S. PATENT DOCUMENTS 5,210,590 A    5/1993  Landa et al.
5,589,351 A    12/1996 Harootunian
(Continued)

FOREIGN PATENT DOCUMENTS

CA    2 218 818 C    8/2007
EP    0 902 271      3/1999
(Continued)

OTHER PUBLICATIONS

International Search Report dated Oct. 7, 2010 corresponding to PCT/GB2010/000028 (4 pages).
(Continued)

*Primary Examiner* — Samuel P Siefke
(74) *Attorney, Agent, or Firm* — Hartman Global IP Law; Gary M. Hartman; Domenica N. S. Hartman

(57) ABSTRACT

An apparatus for detecting spectra in light emanating from chemical or biochemical reactions occurring in at least one reaction vessel (3) of a plurality of reaction vessels is disclosed. Each reaction vessel (3) has a receptacle portion having an emitting area from which light can emanate. The apparatus may include a masking element (5) having an array of apertures (6) through which light from each reaction vessel (3) can escape. A plurality of light waveguides (7) are arranged to guide light from the apertures (6) in the masking element (5) to a light dispersing device (8) for dispersing the light from each waveguide (7) into a dispersed spectrum. A light detecting device (10) detects specific spectra in the dispersed spectra of light substantially simultaneously. In one embodiment, the apertures (6) are substantially smaller in size than the emitting area of the reaction vessel, but in another embodiment, the apertures (6) are substantially
(Continued)

similar in size to the emitting area of the reaction vessel and the light waveguides (7) have a diameter that tapers from a first end substantially similar in diameter to the area of the top of the reaction vessel to a second end that is substantially smaller in diameter. In an alternative embodiment, the light waveguides are not used, when light from the small apertures is directed straight at the light dispersing device. In a further alternative embodiment, several light waveguides are provided for each reaction vessel, each waveguide directing light to a different detector for detecting a different specific spectrum.

25 Claims, 12 Drawing Sheets

(52) U.S. Cl.
CPC .............. *G01N 2201/0826* (2013.01); *G01N 2201/0833* (2013.01)

(56) References Cited

U.S. PATENT DOCUMENTS

| | | | |
|---|---|---|---|
| 5,830,134 | A | 11/1998 | Caputo et al. |
| 6,015,674 | A | 1/2000 | Woudenberg et al. |
| 6,144,448 | A | 11/2000 | Mitoma |
| 6,469,311 | B1 | 10/2002 | Modlin et al. |
| 6,814,934 | B1 | 11/2004 | Higuchi |
| 6,982,431 | B2 | 1/2006 | Modlin et al. |
| 7,136,550 | B2 | 11/2006 | Mozdy |
| 7,715,001 | B2 | 5/2010 | Lundquist et al. |
| 2003/0038248 | A1 | 2/2003 | Maher et al. |
| 2004/0224317 | A1 | 11/2004 | Kordunski et al. |
| 2005/0270527 | A1 | 12/2005 | Reel |
| 2006/0093254 | A1 | 5/2006 | Mozdy |
| 2007/0206187 | A1 | 9/2007 | Lundquist et al. |

FOREIGN PATENT DOCUMENTS

| | | |
|---|---|---|
| EP | 0 953 379 | 11/1999 |
| EP | 0 953 838 | 11/1999 |
| EP | 0 706 649 B1 | 1/2001 |
| EP | 1 191 336 A1 | 3/2002 |
| EP | 2 081 011 A1 | 7/2009 |
| JP | 63-008537 | 1/1988 |
| JP | 63 298137 | 12/1988 |
| JP | S63-298137 | 12/1988 |
| JP | 10-170444 | 6/1998 |
| JP | 10-197449 | 7/1998 |
| JP | 10-293098 | 11/1998 |
| JP | 10-318929 | 12/1998 |
| JP | 2003-522969 | 7/2003 |
| JP | 2005-077260 | 3/2005 |
| JP | 2003-522969 | 7/2013 |
| WO | 93/13423 | 7/1993 |
| WO | 01/59432 | 8/2001 |
| WO | 03/098279 | 11/2003 |
| WO | WO 2005/093393 A2 | 10/2005 |
| WO | WO 2005/118773 A2 | 12/2005 |
| WO | 2008/041524 A1 | 4/2008 |
| WO | WO 2009/027102 A2 | 3/2009 |

OTHER PUBLICATIONS

Burgess et al., "Use of Analytical Fluorescence with Fiber Optics," Progress in Analytical Luminescence,1998, pp. 100-110.

Chien et al., "A novel fluorescence quantification method for polymerase chain reaction system," Optics Communications, 2006, vol. 266, pp. 744-750.

Hanning et al., "A liquid core waveguide fluorescence detector for multicapillary electrophoresis applied to DNA sequencing in a 91-capillary array," Eletrophoresis, 2000, vol. 21, pp. 3290-3304.

Higuchi et al., "Simultaneous amplification and detection of specific DNA sequences," Bio/Technology, Apr. 1992, vol. 10, pp. 413-417.

Karger et al., "Multiwavelength fluorescence detection for DNA sequencing using capillary electrophoresis," Nucleic Acids Research, 1991, vol. 19, No. 18, pp. 4955-4962.

Lee et al., "A novel real-time PCR machine with a miniature spectrometer for fluorescence sensing in a micro liter volume glass capillary," Sensors and Actuators B, 2004, vol. 100, pp. 401-410.

Quesada et al., "Multiple capillary DNA sequencer that uses fiber-optic illumination and detection," Electrophoresis, 1996, vol. 17, pp. 1841-1851.

Simpson et al., "A transmission imaging spectrograph and microfabricated channel system for DNA analysis," Electrophoresis, 2000, vol. 21, pp. 135-149.

Xiang et al., "Miniature real time PCR on chip with multi-channel fiber optical fluorescence detection module," Biomed Microdevices, 2007, vol. 9, pp. 443-449.

Zhang et al., "Two-dimensional direct-reading fluorescence spectrograph for DNA sequencing by capillary array electrophoresis," Anal. Chem., 2001, vol. 73, pp. 1234-1239.

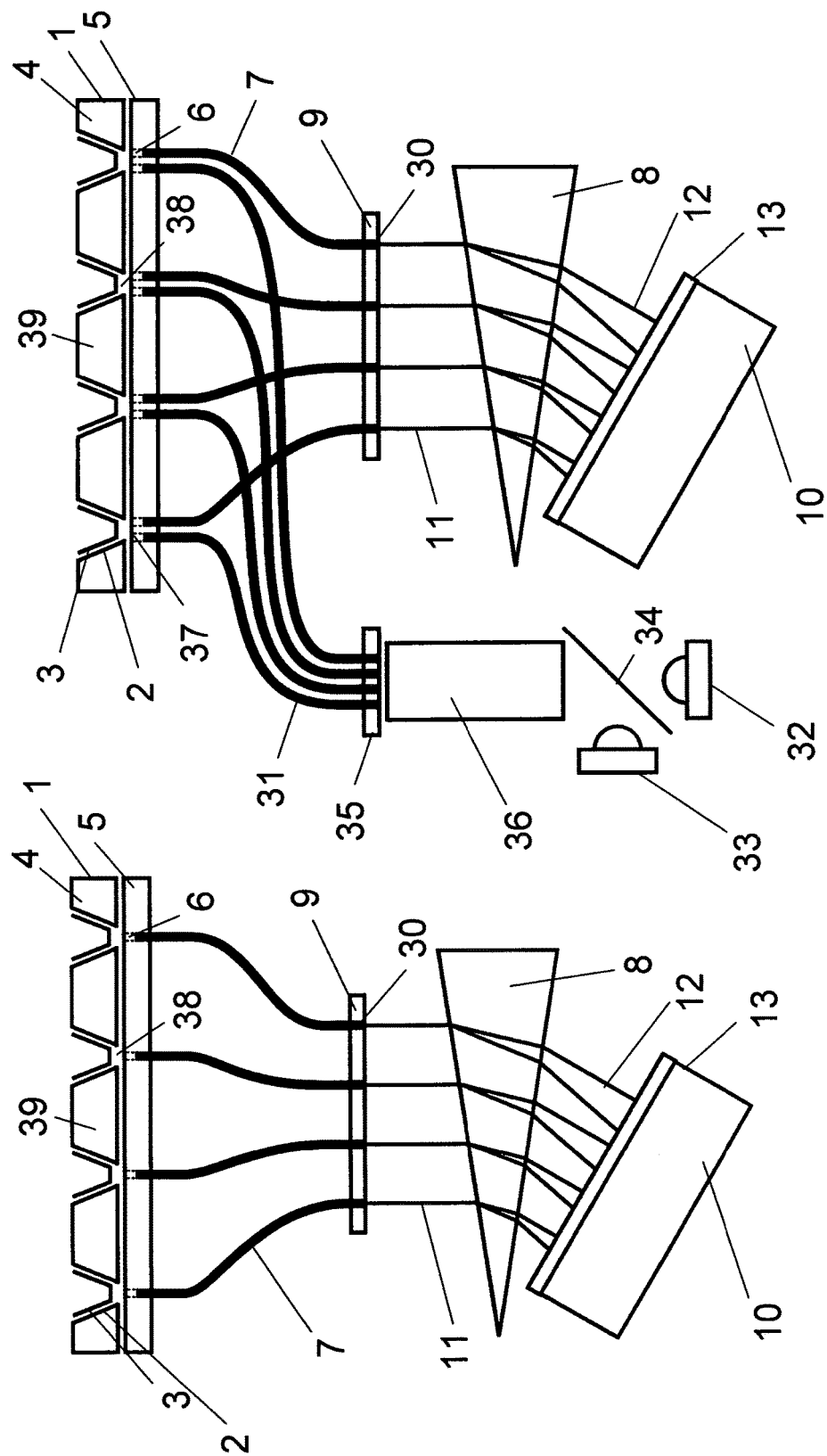

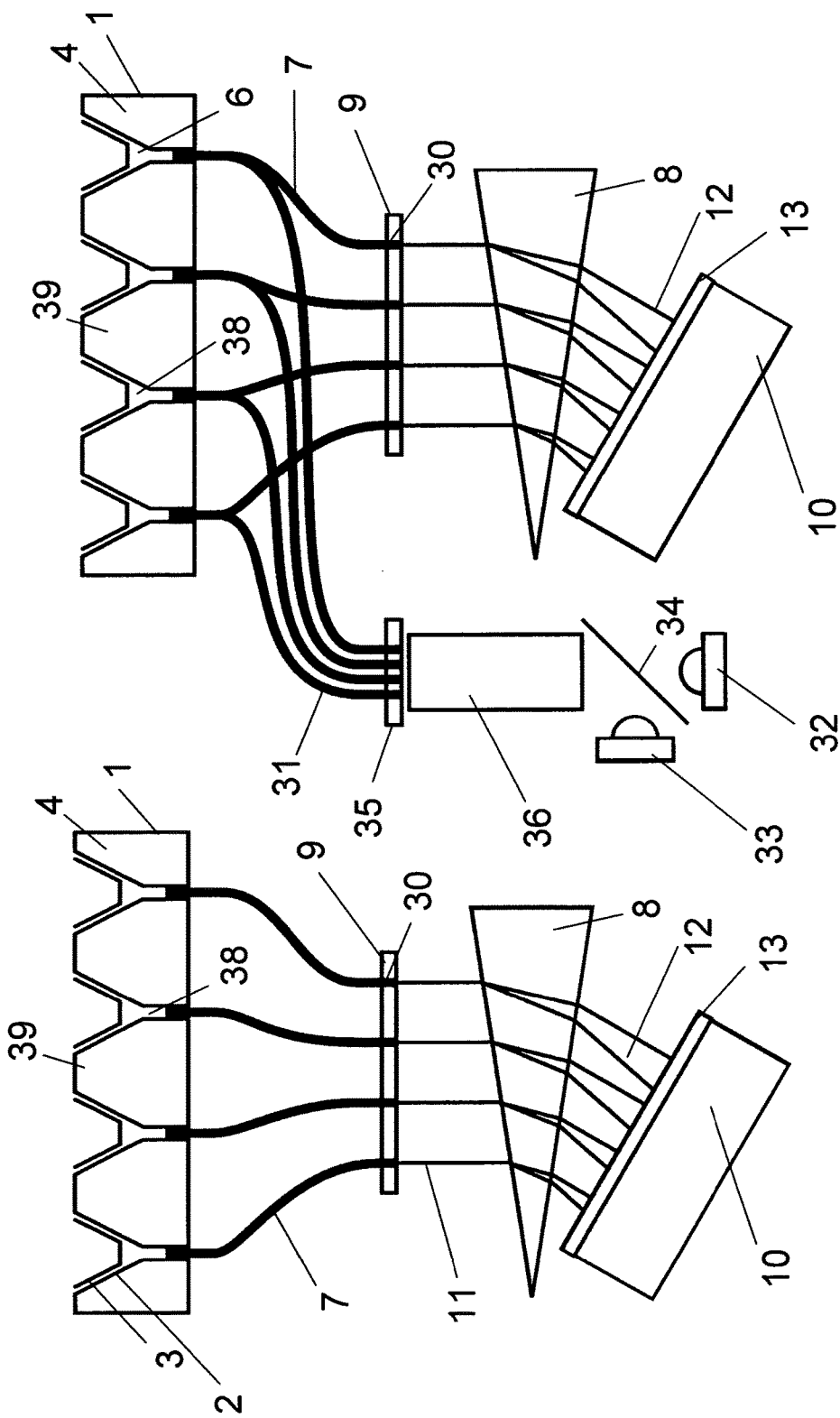

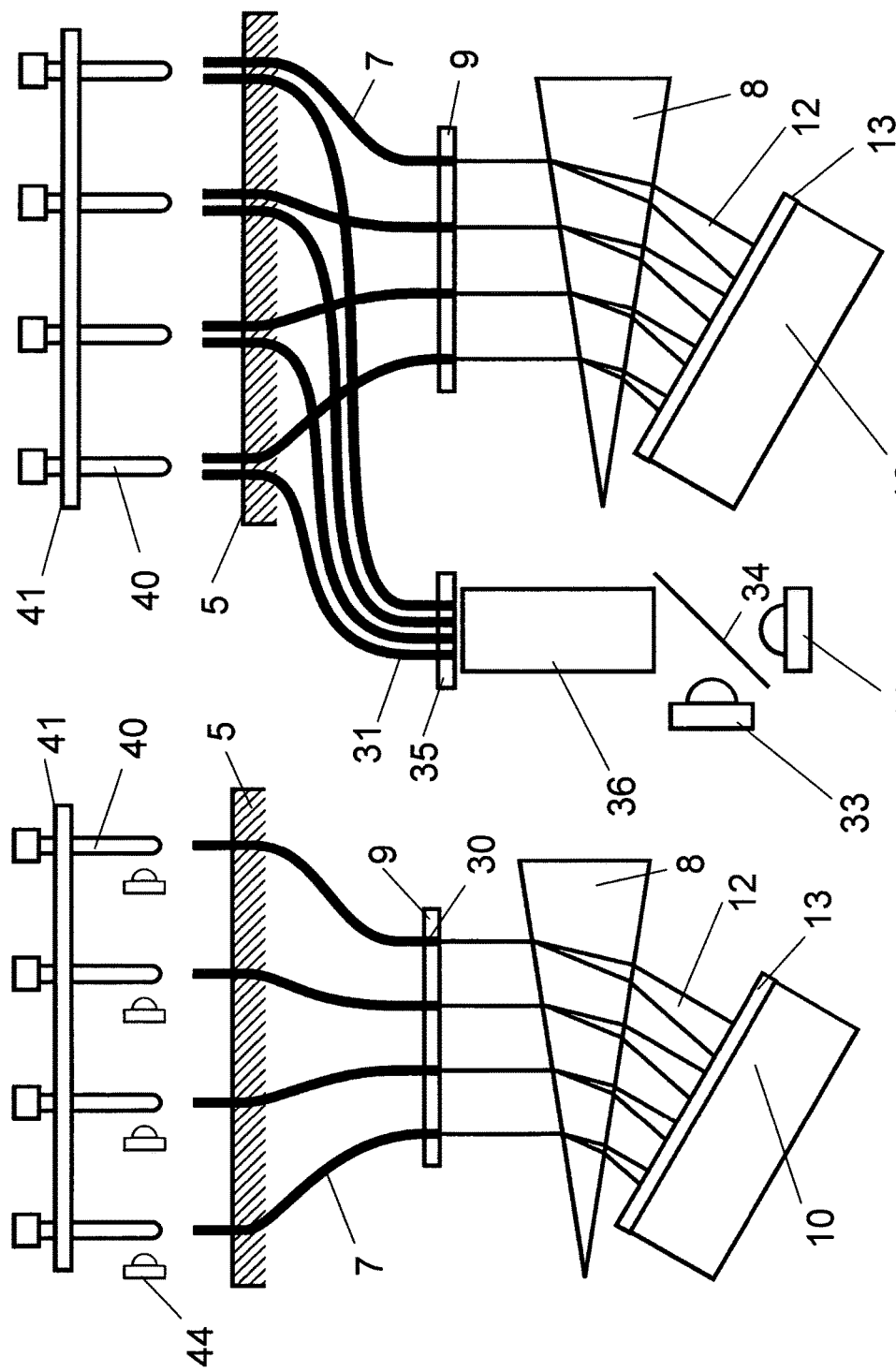

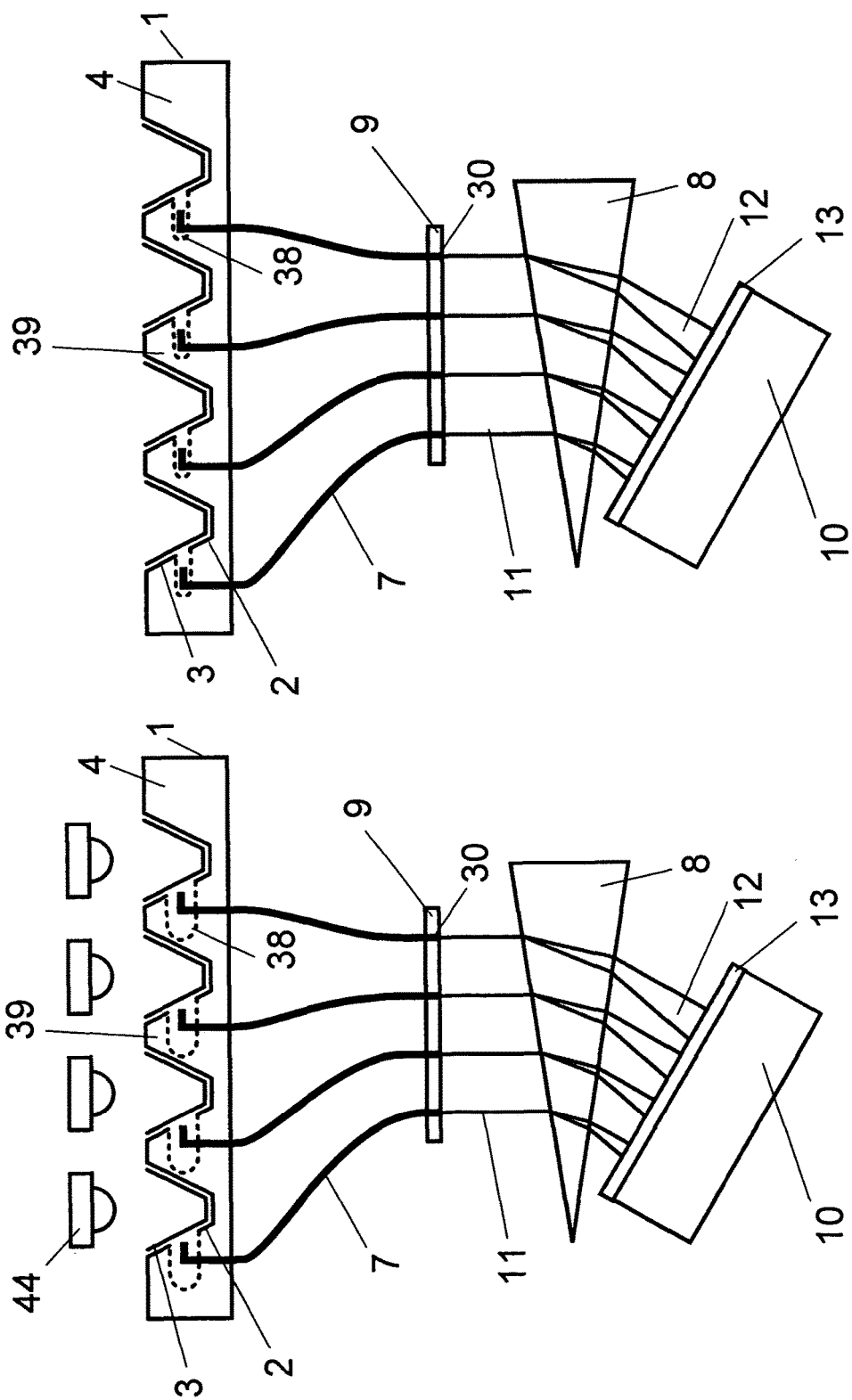

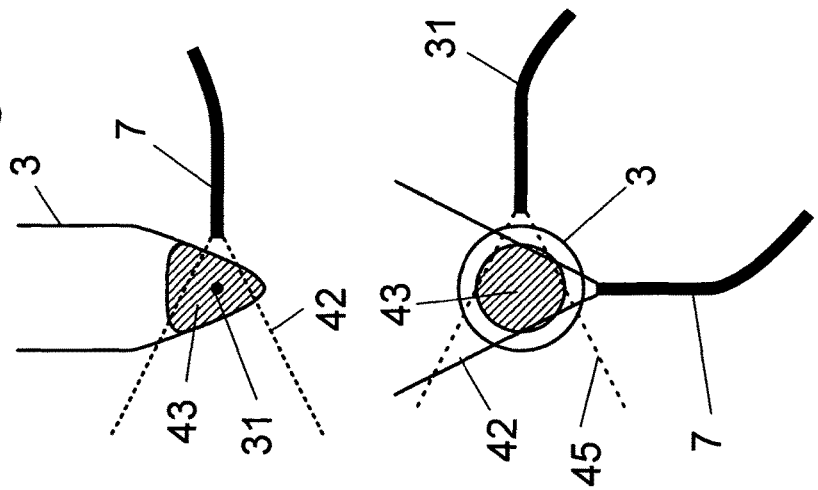
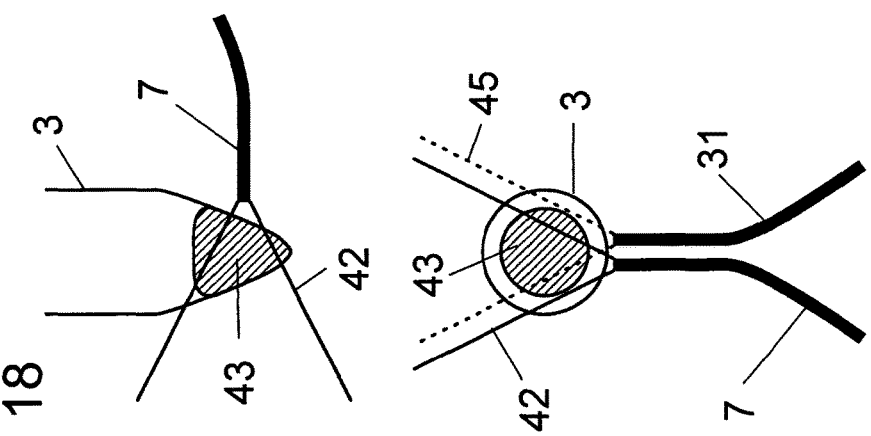
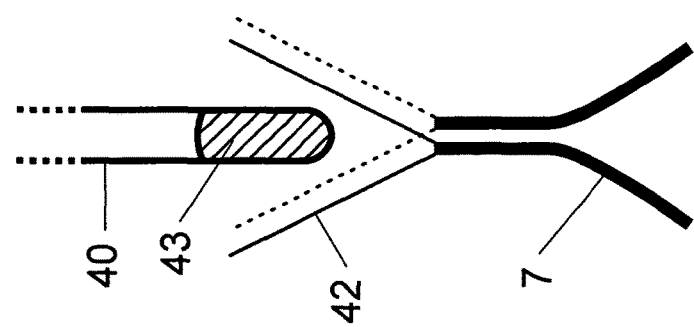

OPTICAL SYSTEM FOR CHEMICAL AND/OR BIOCHEMICAL REACTIONS

The present invention relates to an optical system for monitoring reactions, in particular, though not exclusively, for monitoring light emanating from reaction vessels in which chemical or biochemical reactions are carried out.

Many chemical and biochemical reactions are carried out which produce a detectable light signal, such as a fluorescent, chemiluminescent or bioluminescent signal, which occurs or is modified under certain reaction conditions. Such signals may emanate due to the reagents or results of the reaction(s) emitting light under certain conditions, for example due to excitation energy being applied, or may emanate by being generated by the reaction itself.

Detection of these light signals may be used in a variety of ways. In particular they can allow for the detection of the occurrence of a reaction, which may be indicative of the presence or absence of a particular reagent in a test sample, or to provide information about the progress or kinetics of a particular reaction. Although the term "light" is generally used to include visible light, it will be appreciated that optical signals that can emanate from reactions and be detected may also occur in the infra-red and/or ultra-violet portions of the spectrum and it is intended that the term "light" encompass all optical signals that can emanate from reactions of whatever wavelength that can be detected.

In many instances a reaction mixture may contain more than one "signaling" reagent, and the light signals may need to be detected or monitored over time, in order to provide a full set of information about the occurrence, nature or progress of a particular reaction.

A particular example of a reaction where detectable signals and in particular fluorescent signals are monitored is in nucleic acid amplification techniques and in particular the polymerase chain reaction (PCR). Amplification of DNA by polymerase chain reaction (PCR) is a technique fundamental to molecular biology. PCR is a widely used and effective technique for detecting the presence of specific nucleic acids within a sample, even where the relative amounts of the target nucleic acid is low. Thus it is useful in a wide variety of fields, including diagnostics and detection as well as in research.

Nucleic acid analysis by PCR requires sample preparation, amplification, and product analysis. Although these steps are usually performed sequentially, amplification and analysis can occur simultaneously.

In the course of the PCR, a specific target nucleic acid is amplified by a series of reiterations of a cycle of steps in which nucleic acids present in the reaction mixture are denatured at relatively high temperatures, for example at 95° C. (denaturation), then the reaction mixture is cooled to a temperature at which short oligonucleotide primers bind to the single stranded target nucleic acid, for example at 55° C. (annealing). Thereafter, the primers are extended using a polymerase enzyme, for example at 72° C. (extension), so that the original nucleic acid sequence has been replicated. Repeated cycles of denaturation, annealing and extension result in the exponential increase in the amount of target nucleic acid present in the sample.

DNA dyes or fluorescent probes can be added to the PCR mixture before amplification and used to analyse the progress of the PCR during amplification. These kinetic measurements allow for the possibility that the amount of nucleic acid present in the original sample can be quantitated.

In some systems, sample analysis occurs concurrently with amplification in the same tube within the same instrument. This combined approach decreases sample handling, saves time, and greatly reduces the risk of product contamination for subsequent reactions, as there is no need to remove the samples from their closed containers for further analysis. The concept of combining amplification with product analysis has become known as "real time" PCR.

However, the fact that these systems produce complex and often overlapping signals, from multiple different fluorophores within the system means that complex signal resolution is required to determine the intensity of the signal from the individual fluorophores.

The complexity is further compounded in that PCRs are generally conducted in specifically constructed thermal cycles, such as block heaters, which accommodate arrays of multiple reaction vessels at the same time. These are then cycled together, and the signals produced by each vessel monitored.

Current systems for PCR fluorimetry often rely on detection systems such as monochrome detectors (CCD, photodiode, PMT, CMOS detectors etc.) which on their own will only detect the presence or absence of light, but cannot distinguish amongst light of different wavebands or colours. Therefore they are not able directly to differentiate between the various different fluorophore signals. This problem is often addressed by having an external means of separating or filtering light into different wavebands for detection at different points on the detector, or at different points in time.

These external means increase the cost, size and complexity of the instrument. Such external means often need to be precisely mounted for optical alignment, and this tends to reduce the robustness of the instrument or leads to increased size, weight and cost associated with the mounting.

Many useful applications of PCR analysis rely on readings from multiple wavebands, and all require each vessel used to be measured, so if the optical apparatus of an instrument requires reconfiguration to read different wavebands or vessels the time taken to acquire a sequence of readings is inevitably increased (for example, movement of a filter wheel, or scanning of an optical system between wells will introduce an inevitable delay, and in any case if acquisitions are not concurrent they will take longer). This has the effect of reducing the maximum rate of acquisitions, and hence reducing time resolution of measurements, which can be critical when the acquisitions are taken during a process such as a temperature ramp for the purposes of melt analysis.

It would therefore be useful to have a way of being able to distinguish and detect different wavelengths of light emanating from a number of different reaction vessels at the same time.

Accordingly, in a first aspect of the present invention there is provided apparatus for detecting spectra in light emanating from chemical or biochemical reactions occurring in at least one reaction vessel of a plurality of reaction vessels, each reaction vessel comprising a receptacle portion having an emitting area from which light can emanate, said apparatus comprising a masking element having an array of small apertures through which light can pass, each small aperture being substantially smaller than the emitting area of the receptacle portion of the reaction vessel, there being one or more small apertures arranged adjacent each of the reaction vessels, and a light detecting device for detecting the spectra in the light emanating from the chemical or biochemical reactions via the array of small apertures substantially simultaneously.

As used herein, the expression "reaction vessel" refers to any form of support or container in which the reaction may be carried out. Thus, it includes reaction tubes, wells in reaction plates as well as slides or chips.

Generally, the spectrum will be characteristic of a particular reagent such as a dye which is present in the chemical or biochemical reaction, and so the presence or absence, or intensity of the signal having that characteristic spectrum may be indicative of a property or state of the reaction mixture.

As used herein, the expression "chemical or biochemical reaction" includes various operations in which reagents may react together in order to produce new or different reagents or products, and also the treatment of samples to determine the changes which take place in reagents under changing conditions, such as temperature, electrochemical potential or time. Thus the expression includes operations such as melting point analysis of reagents, as well as reactions such as the PCR.

In one embodiment, the apparatus further comprises a light dispersing device for dispersing the light that escapes from the small apertures in the masking element into a dispersed spectrum. The light dispersing device may be a light diverging device, such as a prism or a diffraction grating.

The apparatus may further comprise a plurality of light waveguides arranged to guide light from the small apertures in the masking element to the light dispersing device.

In one embodiment, the light detecting device comprises a plane onto which the dispersed spectra of light from the apertures are produced, and one or more detectors for detecting specific spectra within the dispersed spectra.

The light dispersing device may comprise a light splitting device for dispersing the light into different wavebands.

The apparatus may comprise a plurality of light waveguides arranged to guide light from the small apertures in the masking element to the light detecting device.

In an embodiment, the masking element comprises at least two small apertures per reaction vessel, each of the plurality of light waveguides being arranged to guide light from a respective small aperture to the light detecting device, wherein one waveguide per reaction vessel guides the light to one portion of the light detecting device for detecting one specific spectrum of the light and another waveguide per reaction vessel guides the light to another portion of the light detecting device for detecting one specific spectrum of the light.

In this embodiment, the different portions of the light detecting device may comprise light sensors sensitive to different spectra of the light.

Filters may be arranged between the light waveguides and the different portions of the light detecting device, each respective filter passing a different spectrum of the light to the respective portion of the light detecting device.

Depending on the other elements of the apparatus, there may be other benefits—for example the simultaneous acquisition of each waveband from the or each vessel means that in systems where there may be fluctuations in the excitation source, each waveband and vessel will be acquired at the same excitation level. Any physical changes in the vessel, such as vessel movement or bubble formation, condensation or movement of contents will affect each waveband acquisition equally. This is a considerable benefit in cases where levels of one (often passive) dye are used to normalise levels of another (often active) dye.

Since there is no need to alter the acquisition wavebands or vessel/detector alignment, for example by physical movement, the detector can acquire data with minimal interruption. Since the detector can acquire all available wavebands just as easily as any subset of wavebands, there is no need to work with a reduced waveband set, and this increases opportunities for later analysis. Physical alignment within the machine is also rendered less critical, since the detector only needs to be aligned to the vessels, rather than to external filters etc., and any minor misalignment can be corrected for by processing of the detector image, for example pattern recognition and/or registration marks.

In order to generate a detectable signal from a chemical or biochemical reaction, for example using fluorescent signaling reagents, it is frequently necessary to illuminate the reaction mixture in order to provide light energy, for example for the fluorophore to absorb, so as to allow it to emit light at its characteristic spectrum.

The signals may be monitored continuously or taken as certain particular time points during each thermal cycle only, so that the changes over cycle number can be seen.

According to a second aspect, the invention provides an apparatus for detecting spectra in light emanating from chemical or biochemical reactions occurring in at least one reaction vessel of a plurality of reaction vessels, each reaction vessel comprising a receptacle portion having an emitting area from which light can emanate, said apparatus comprising a masking element having a small aperture adjacent each reaction vessel through which light from that reaction vessel can pass, a plurality of light waveguides arranged to guide light from the small apertures in the masking element to a light dispersing device for dispersing the light from each waveguide into a dispersed spectrum, and a light detecting device for detecting spectra in the dispersed spectra of light substantially simultaneously.

As mentioned above, the light dispersing device may comprise a prism or a diffraction grating.

The apparatus may further comprise an output array element having a plurality of output apertures arranged in a predetermined array adjacent the light dispersing device, wherein each respective light waveguide comprises a first end constrained to receive light from a respective small aperture in the masking element and a second end constrained at a respective aperture in the array element to direct light to the light dispersing device.

The light detecting device may comprise a plane onto which the dispersed spectrum of light from each aperture is produced, and one or more detectors for detecting specific spectra within the dispersed spectra. The plane may be a sensing surface of the detector, or may be an image plane on an optical element of the detector, which may contain suitable optics to image the plane onto a sensing surface.

The array of output apertures in the output array element may be arranged so that the dispersed spectra on the plane of the light detecting device do not overlap, at least within the spectral range where there is significant light emitted from the vessels and passed to the sensor, and where the sensor has significant sensitivity. It will, of course, be apparent that the spectra could be considered to extend from deep UV to far infrared, and these wavelengths will overlap, but light at these wavelengths can effectively be ignored where it is not expected to be emitted, and/or the optics (e.g. prism) may well not transmit it, and/or the sensor is not significantly sensitive to it. Even so, there may be filters over the sensor to block IR etc.—this means there is no effect if the IR portion of one spectrum overlaps another spectrum, since the sensor won't detect the overlapped IR light. The arrangement may also be chosen to efficiently use the plane of the light detecting device, for example to match its aspect ratio, and provide only just enough space between the dispersed spectra to substantially prevent crosstalk between the spectra). Such an arrangement can improve the signal to noise ratio of measurements by providing for readings across a greater area of the plane.

In one embodiment, the array of output apertures in the output array element has a smaller area than the array of small apertures corresponding to the array of reaction vessels.

The apparatus of any embodiment may also comprise a further light waveguide for each reaction vessel arranged between a further small aperture in the masking element adjacent each reaction vessel and an excitation light source for guiding light from the excitation light source to each of the reaction vessels.

There may be a plurality of excitation light sources, which may provide excitation light of the same or different spectra, the excitation light from each excitation light source being guided to each of the reaction vessels via one or more further light waveguides.

Thus, multiple excitation light sources may be provided, arranged so that each source directs light into the further light waveguides. Alternatively, multiple further light waveguides may be provided to each reaction vessel, each guiding excitation light from one or more excitation light sources.

Suitable excitation light sources include UV, Halogen, Xenon or fluorescent lamps, Light Emitting Diodes, Lasers, or some combination of these sources. This excitation causes fluorescent dyes or markers which are contained with the reaction vessel to emit light with a characteristic spectrum in the range of the spectrum suitable for the detector type, and this can then be picked up by the detectors.

Excitation light sources are preferably restricted to regions of the spectrum that are distinct from the most informative emitted wavelengths, for example the peak emission wavelengths of any fluorophores, reducing need for filtering and allowing use of a greater portion of the spectrum without interference from reflected excitation. For example, ultraviolet and blue excitation light sources are useful since most commonly used fluorophores emit at longer wavelengths.

The channeling of multiple excitation light sources into the same waveguide can be achieved for example by use of a dichroic mirror arranged to transmit light from one light source positioned so as to emit light directly into the waveguide, and reflect light into the waveguide from another source arranged to emit light perpendicular to the waveguide.

Multiple sources of the same spectrum may be used to increase the power of excitation light, or sources of different spectra may be used, for example where each source is designed to provide acceptable excitation for a specific set of fluorophores. Where multiple sources are provided, they may be individually controlled (in terms of intensity and spectrum) so that acquisitions may be made in the presence of a controlled excitation spectrum. For example, a common application would be the acquisition of emitted fluorescence from FAM and VIC dyes, where a blue LED with appropriate filter provides excitation matched to the FAM dye, and a green LED with appropriate filter provides excitation matched to the VIC dye. By illuminating just the blue LED when acquiring spectra from the FAM dye, a better reading can be made since the green LED excitation light will not be present to interfere with the FAM emission at similar wavelengths. The green LED alone can then be illuminated to acquire a spectrum from the VIC dye.

The apparatus may also comprise one or more additional light waveguides arranged to guide light from one or more excitation light sources to the output array element, without illuminating any reaction vessel. Such a light waveguide may also include a filter, for example a neutral density filter to reduce the intensity of light directed from the excitation light sources to the output array element. These additional lightguides provide for the excitation sources to have their intensity and spectra measured in the same way and at the same time as the light emitted and reflected from the reaction vessels. This provides for example for ratiometric measurement, where the emitted light from the reaction vessels is compared to the spectrum and intensity of the excitation source to yield a more accurate measurement having reduced influence from any variation in the excitation source intensity and spectrum.

The at least one reaction vessel is preferably formed in a generally tapered configuration and may be formed by a capillary.

Preferably, the emitting area is at a top of the receptacle portion, although it may be at a side of the receptacle portion and or at a bottom of the receptacle portion.

The masking element may be provided by a thermal mount in which the array of reaction vessels is mounted.

In another aspect, the invention provides an apparatus for detecting spectra in light emanating from chemical or biochemical reactions occurring in a plurality of reaction vessels of an array of reaction vessels, each reaction vessel comprising a receptacle portion having an emitting area from which light can emanate, said apparatus comprising a at least one light waveguide per reaction vessel being arranged to guide light from the emitting area to a light dispersing device for dispersing the light from the waveguide into a dispersed spectrum, and a light detecting device for detecting spectra in the dispersed spectra of light substantially simultaneously, and at least one excitation arrangement for providing excitation light to the receptacle portion of the reaction vessel.

Preferably, the excitation arrangement comprises a second light waveguide per reaction vessel for guiding excitation light from an excitation light source to the receptacle portion of the reaction vessel.

The excitation arrangement preferably comprises an excitation light source arranged in or adjacent the receptacle portion of the reaction vessel.

The excitation light source preferably comprises a Light Emitting Diode (LED).

The light dispersing device may comprises a prism or a diffraction grating.

Preferably, the emitting area is at a top of the receptacle portion, and/or at a side of the receptacle portion and/or at a bottom of the receptacle portion.

The light detecting device may comprises a CCD or CMOS detector.

The plurality of reaction vessels may be contained within a multi-well plate, such as a 48, 96 or 384 well plate.

The apparatus may further comprise a thermal cycler having a block heater for holding the multi-well plate.

The specific spectrum may be characteristic of a particular reagent or state of a particular reagent within a reaction vessel and/or may be derived from a single species of fluorophore, present in the reaction.

In a preferred embodiment, the chemical or biochemical reaction is a polymerase chain reaction (PCR) conducted in the presence of at least one fluorophore, which may be one or more fluorophores taken from the group including:

fluorophores which intercalate with nucleic acid, such as intercalating dyes;
fluorophores which hybridize with nucleic acid, such as labeled hybridization probes;
fluorophores which are modified by the PCR process, such as labeled digestion probes;
fluorophores which provide for fluorescent energy transfer between them, such as
fluorescent labeled probes; and
other fluorescent probes.

The fluorophore is preferably a fluorescent label attached to a first oligonucleotide probe which specifically hybridizes to a target nucleic acid sequence of the PCR and wherein the first oligonucleotide probe contains a second fluorophore, which is able to exchange fluorescent energy with said fluorescent label when present together on the probe, wherein a polymerase having 5'-3'exonuclease activity is utilized in the PCR so as to digest any first probe bound to target nucleic acid during an extension phase of the reaction.

If necessary, a cooling or refrigeration device may be provided for cooling the light detecting device, particularly when this is a CCD, to increase signal to noise ratio and achieve more accurate readings.

Various embodiments of the invention will now be more fully described, by way of example, with reference to the accompanying diagrammatic drawings, of which:

FIG. 8 shows a schematic diagram, similar to FIG. 1, but in an alternative configuration;

FIG. 9 shows a schematic diagram, similar to FIG. 8, but including excitation in the optical system, similarly to the system of FIG. 7;

FIG. 10 shows a schematic diagram of another embodiment of an optical system for detecting light in a PCR system;

FIG. 11 shows a schematic diagram, similar to FIG. 10, but including excitation in the optical system;

FIG. 12 shows a schematic diagram of a further embodiment of an optical system for detecting light in a PCR system;

FIG. 13 shows a schematic diagram, similar to FIG. 12, but including excitation in the optical system;

FIG. 14 shows a schematic diagram of a still further embodiment of an optical system for detecting light in a PCR system;

FIG. 15 shows a schematic diagram, similar to FIG. 14, but without separate excitation LEDs;

FIG. 16 shows an enlarged view of part of the system of FIG. 13;

FIG. 17 shows a similar enlarged view to that of FIG. 16, but for part of the system of FIG. 15;

FIG. 18 shows a plan view corresponding to FIG. 17;

FIG. 19 shows a similar view to that of FIG. 17, but in an alternate configuration; and FIG. 20 shows a plan view corresponding to FIG. 19.

Figure 1:
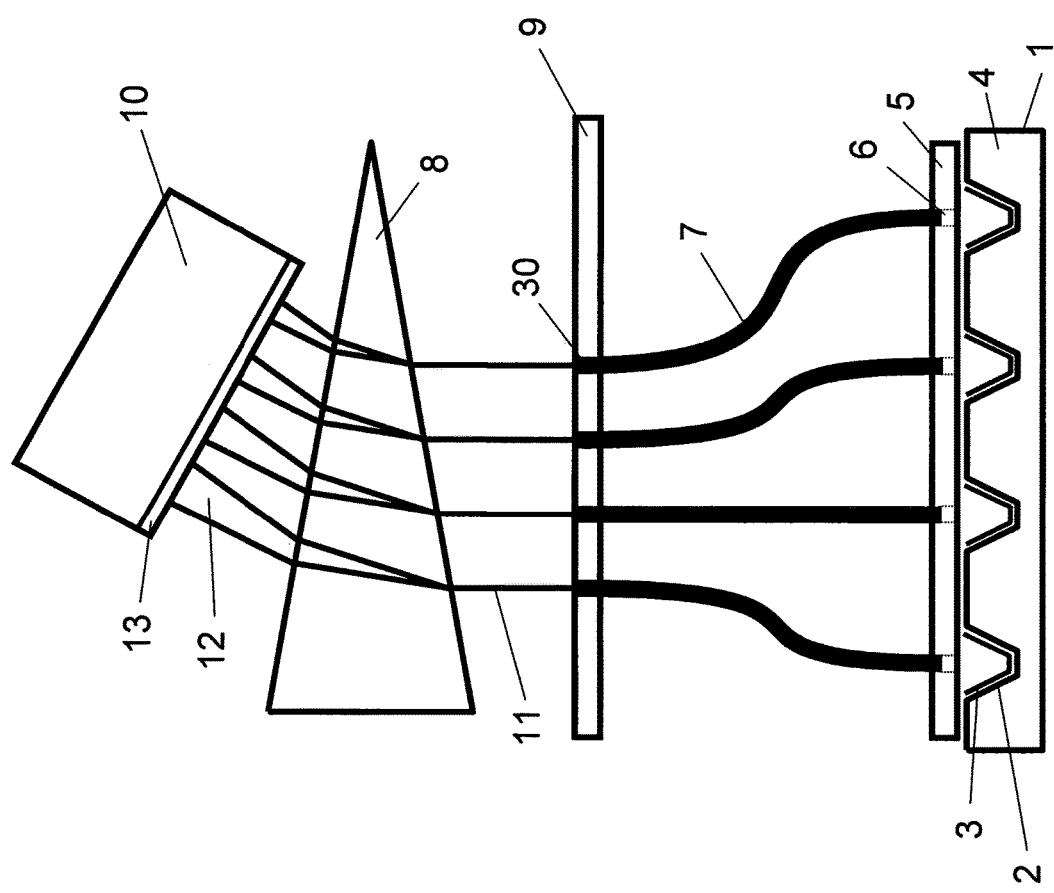
FIG. 1 shows a schematic diagram of a first embodiment of an optical system for detecting light in a PCR system.

Thus, turning first to FIG. 1, there is shown a multi-well array 1 having a number of wells 2 in which are provided reaction vessels 3. The array 1 may well have any number of wells, for example, 48, 96 or 384 as in conventional such arrays. The array 1 may be housed in a heater block 4 of a thermal cycler, as is well known in the field.

As will be apparent to a person skilled in this field, the reaction vessels 3, after having the desired reagents inserted therein, may be sealed and may have a heated lid placed on it. The seal is usually of transparent plastics material which is adhered to the rim of the reaction vessel and the heated lid, which is usually arranged so as to provide pressure on the seal at the rim of the reaction vessel, and heated to reduce condensation on the inside of the seal is also usually transparent or provided with appropriate apertures to allow light from the reaction vessel to escape. These elements are not shown since they are not part of the invention and are well known.

Figure 5:
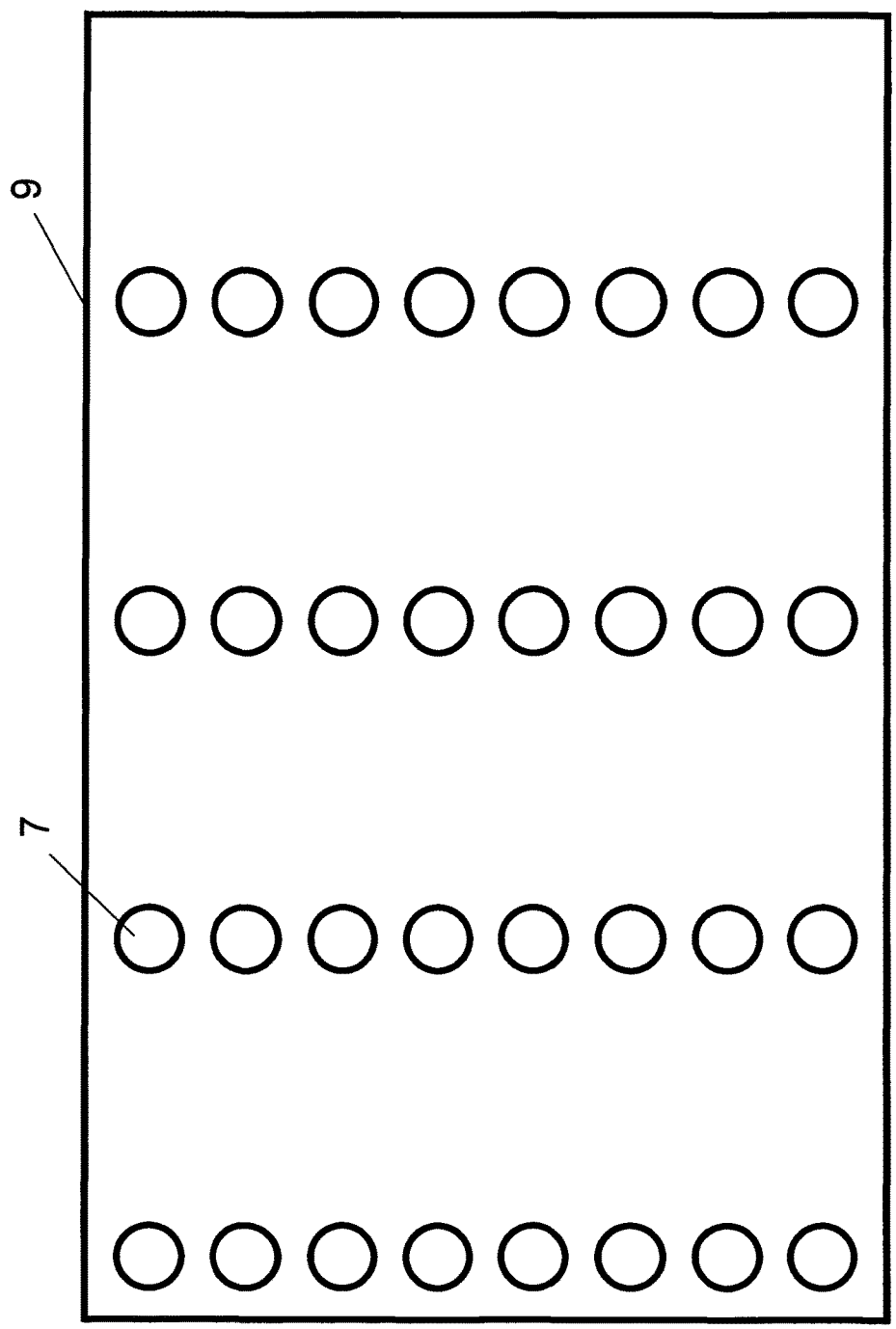
FIG. 5 shows a plan view of an array plate used in the embodiment of FIG. 1.

As shown in FIG. 1, a masking plate 5 is provided, which would be positioned over the heated lid and/or seal, if present. The masking plate prevents light from escaping from the reaction vessels 3, except for through small apertures 6 positioned in the masking plate 5 so as to correspond to the approximate centre of each reaction vessel 3, thereby ensuring that the maximum amount of light will impinge on the small aperture 6. Inserted into each of the small apertures 6 is an optical fibre 7, which guides the light emanating from the reaction vessels towards a light dispersing element, such as a prism 8. One end of each of the optical fibres 7 is mounted in or at the small aperture 6 and the other end is mounted in or at an aperture 30 provided in an array plate 9, as shown in FIG. 5. It will be apparent that the optical fibres 7 guide the light from each of the reaction vessels and direct it in a predetermined array towards the prism 8. The arrangement of the predetermined array of apertures 30, as best shown in FIG. 5, effectively rearranges the array of light from a large array, which may be roughly square in shape if the reaction vessels 3 have approximately the same width as length, into an array where the end of the fibres are more closely packed together in one dimension (vertically in FIG. 5) than in the other direction (horizontally in FIG. 5). It is also possible to provide for the masking plate 5 to be heated, for example by passing a current through resistive elements, and hence also function as a heated lid, if desired. In this case the fibres are preferably chosen to be resistant to the temperatures required of the heated lid.

Figure 6:
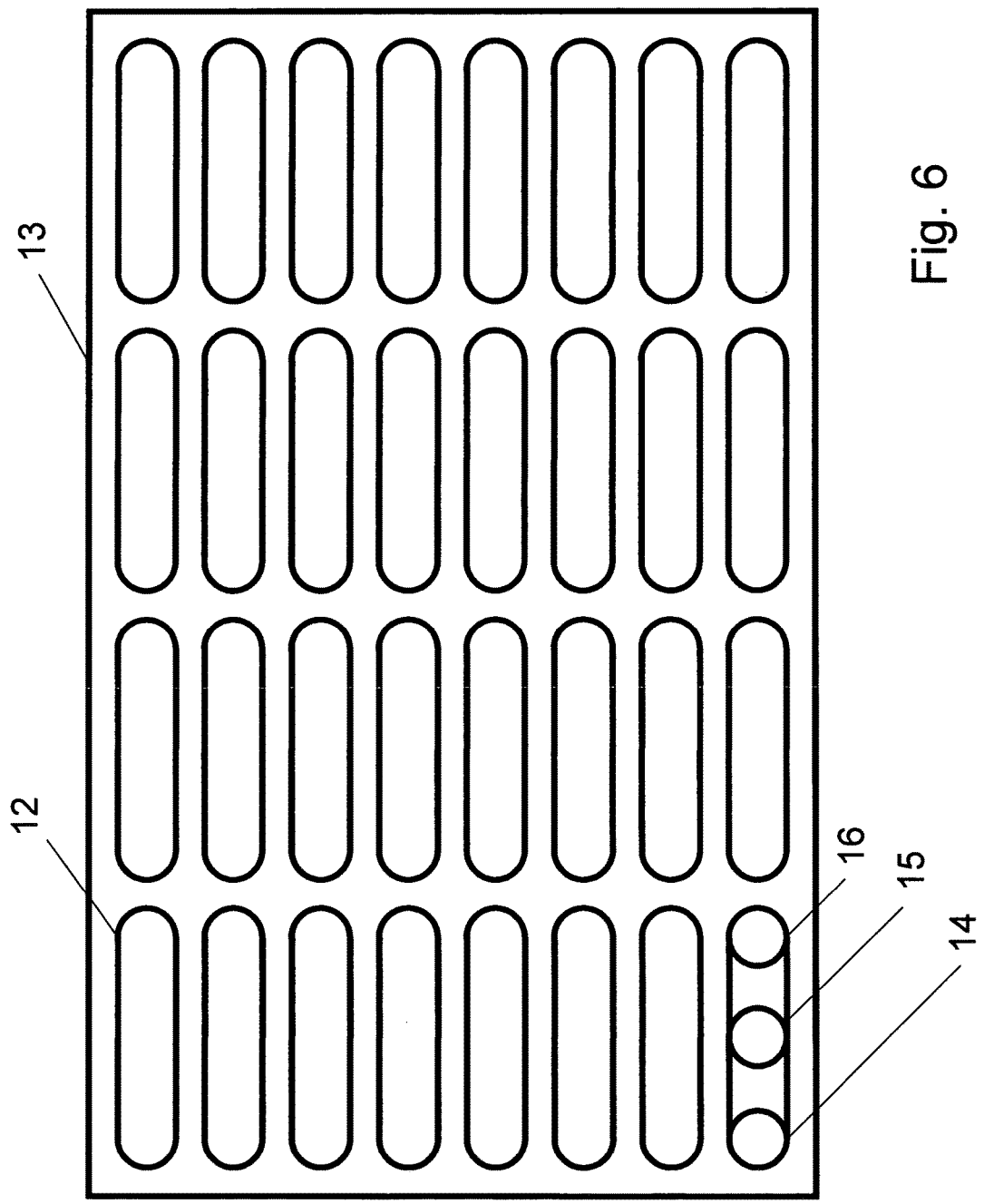
FIG. 6 shows a plan view of an image area in the embodiment of FIG. 1.

Thus, light from the ends of the optical fibres 7 in the array plate 9 is directed along light path 11 to the prism 8 (or other light dispersing element, such as a diffraction grating), which disperses the light from each fibre 7 (and therefore from each reaction vessel 3) into a full spectrum 12, as shown schematically in FIG. 1, into a detector 10. The full spectra are imaged onto an image plane 13, as shown in FIG. 6 in the detector 10. In this way, full spectra of the light emanating from all the reaction vessels are provided simultaneously at the detector 10. It will thus be seen that the spacing of the array in array plate 9 is chosen so that spectra 12, when dispersed by the prism 8 onto the image plane 13 in detector 10, are relatively tightly packed in one direction, so that the height of the spectra are reasonably spaced, and are spaced sufficiently in the other direction so that the dispersed spectra do not overlap. Since the small apertures are substantially smaller in diameter than the size of the top area of the reaction vessels, the array of apertures in the array plate 9 (and the array of full spectra 12 in image plane 13) can be smaller than the size of the array 1 of reaction vessels 3.

The detector 10 may, in one embodiment, consist of a ½" (12 mm) monochrome CMOS sensor, together with appropriate electronics and software allowing a "raw" frame to be captured giving the actual measured light levels for each pixel. This is used with a megapixel photographic lens assembly to form a camera which can focus light from a plane in space onto the sensor chip. It should be noted that "lens" is used herein interchangeably to mean either an "optical lens", a single piece of glass, or a "photographic lens"/"lens assembly" meaning one or more lenses used as a set to image onto a sensor plane such as the CMOS sensor. The camera is then used to image through a simple single glass lens and a 30° uncoated glass prism onto the fibre array.

Sensors providing for global shutter control giving substantially equivalent exposure intervals for each pixel are well suited for use with the system, since exposure of the entire image over the same time period means that each channel of each spectrum in that image is affected in the same way by any time varying conditions such as variable excitation intensity, etc. For each reaction vessel, each channel is also affected equally by any time varying conditions in the reaction vessel, such as condensation, temperature, physical movement such as bubble formation and movement etc.

Sensors that are well suited for use with the system include those providing for different subsets of pixels across the sensor array to be captured with different parameters, for example, electronic parameters such as analogue gain and offset, ADC reference voltage, pixel potential barrier, and other commonly controlled capture settings. Examples include sensors such as the Micron MT9T001, where pixels are grouped into 2×2 blocks, where the top left pixels of each block all belong to one subset, the top right pixels belong to another subset, and similarly for the bottom left and bottom right pixels. Each of these subsets of pixels can have a different ADC gain parameter. This can be used to effectively extend the dynamic range of the sensor; for example if a gain of 4× is used on even rows of the image, and a gain setting of 8× is used on odd rows, the spectral image will effectively be acquired as two half resolution images with different gain levels, where the lower gain image has a higher maximum light level at saturation, and the higher gain image provides greater precision at low light levels. Another example is the Aptina/Micron MT9V024 image sensor, where the image can be divided into an array of rectangular regions, and each rectangular region can have individual digital gain and gain control settings. The spectral image is particularly suitable for a sensor having different gain in different regions, since the regions can be arranged to coincide with the spectral images, giving different gain settings for different areas of the spectra, and hence for different wavelength regions. This can be used to acquire regions of the spectra that have different intensity levels so as to give the best SNR and least quantization noise for each region.

Sensors providing a non-linear response in terms of output codes to light level are well suited for use with the system, particularly where the sensor response can be programmed, for example by means of multiple linear response regions and/or compounding. An example of such a sensor is the Aptina/Micron MT9V024, which can use 12 bit to 10 bit compounding, and can also be given up to 3 regions if different linear response, resulting in a greater dynamic range. For example, such sensors can be configured so that they yield higher light to output gain at low light levels, giving good SNR and sensitivity at the light levels associated with early cycle PCR amplification where measurement precision is critical, but then yield lower gain at the higher light levels associated with mid and late cycle PCR in the plateau phase, where measurement precision is less critical. A final region of even lower gain at very high light levels associated with reflection of the excitation light can then be used to allow for measurement of the reflected light without the saturation that would result from a uniform higher gain level.

As shown in FIG. 6, by providing a full spectrum 12 of dispersed light from each reaction vessel at the same time, the detector 10 can detect any desired specific spectrum within the full spectrum. Thus, FIG. 6 shows three wavebands (corresponding to the colours red 14, green 15 and blue 16) within a full spectrum 12, that can be detected, as desired. Of course, particular wavelengths can also be detected, if desired, as can other wavebands. Each full spectrum 12 in the image plane 13 can be scanned by the detector and monitored and analysed, as required by time and wavelength according to the requirements of the particular analysis being carried out, as will be apparent to a person skilled in the field.

In one alternative embodiment to that described above, the apertures 6 need not be small relative to the area of the top of the reaction vessel, but can be made of substantially similar size thereto. In this case, the end of each of the optical fibres 7 that is mounted in or at the aperture would be of substantially similar size and the diameter of the fibre would taper down to a smaller diameter, which would be that at the other end mounted in or at aperture 30 provided in array plate 9. It will be apparent that this embodiment has the advantage that substantially all the light emanating from the reaction vessels would be captured by the large diameter end of the optical fibres and would then be "concentrated" as it passes through the tapering portion of the fibre. Between the array plate 9 and the detector 10, the system would be the same as described above, so that both embodiments have the advantage that the signals from the array of reaction vessels are rearranged into a format more suitable for passing through the prism and to the detector, i.e. that the overall size of the "image" passed from the array plate is smaller in overall size, than that of the array plate itself.

For example, in a direct image of the array of vessels taken from above, only about ¼ (or more) of the plate image area would normally have a substantial amount of emitted light from the vessels—the remaining ¾ of the image is of the area between the vessels. When the masking element and the fibres are placed between the array of vessels and the detector and the emitted light is rearranged as explained above, the resulting image is smaller than a direct image would be, allowing for the whole image (i.e. the light from all the vessels in the array) to be passed through the prism and on to the detector, even though less of the resulting image actually shows emitted light (for example, the system may actually have only about ¹⁄₁₀th of the area illuminated) so as to leave the necessary space for the well spectra to be dispersed without overlapping.

Figure 2:
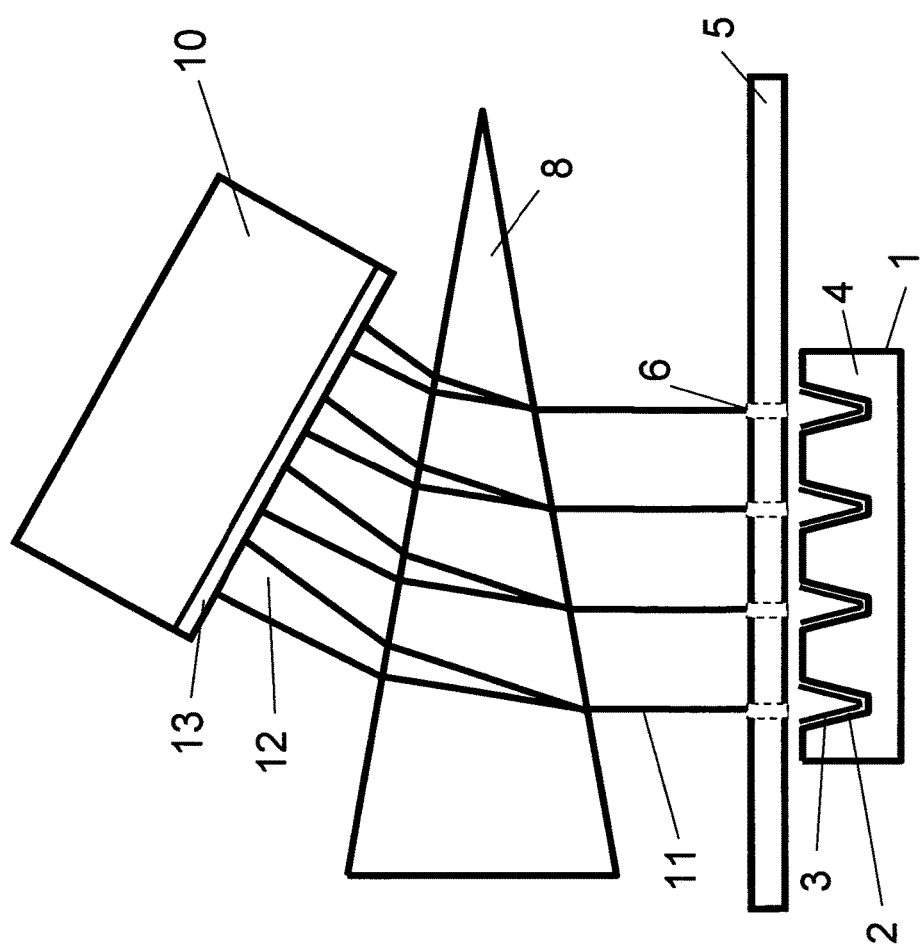
FIG. 2 shows a schematic diagram of a second embodiment of an optical system for detecting light in a PCR system.

Other embodiments of the invention will now be described, with the same or similar elements as described above with respect to FIGS. 1, 5 and 6 being given the same reference numbers. Thus, as shown in FIG. 2, a second embodiment of the invention has the same elements as the embodiment of FIG. 1, except that the optical fibres 7 are not required. In this case, if the array 1 of reaction vessels 3 is not too large, it may not be necessary to compress the array of full spectra imaged onto the image plane 13 of the detector 10. In this case, however, the masking plate 5 is still used to block most of the light emanating from the reactions in the reaction vessels 3, and to only allow beams 11 of light of much smaller diameter to pass through the small apertures 6 in the masking plate 5 to the prism 8 and on to the image 13. This is so that the full spectra 12 are prevented from overlapping on the image plane 13, which would otherwise be the case if light from the complete top area of each reaction vessel 3 were to be dispersed by the prism.

Figure 3:
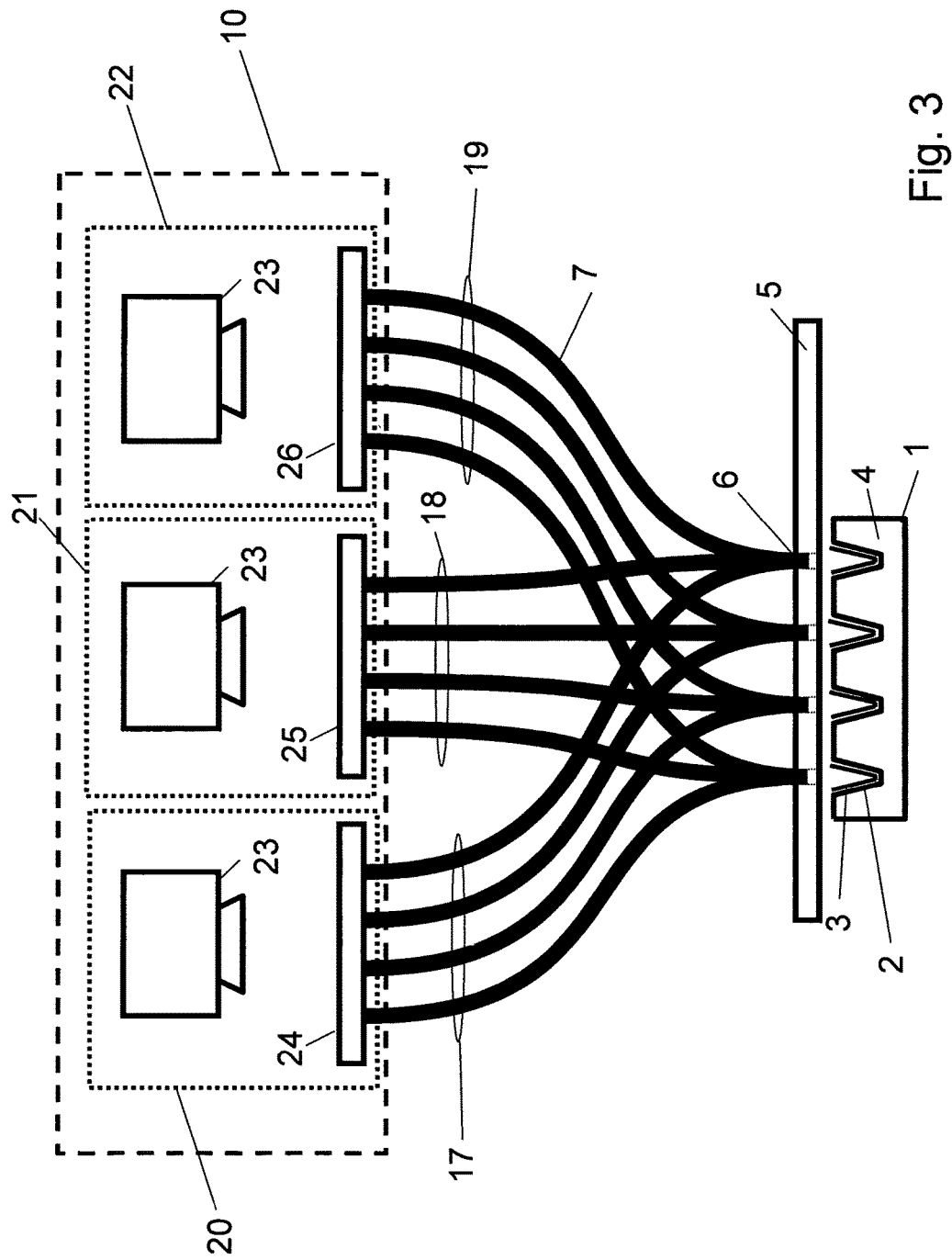
FIG. 3 shows a schematic diagram of a third embodiment of an optical system for detecting light in a PCR system.
Figure 4:
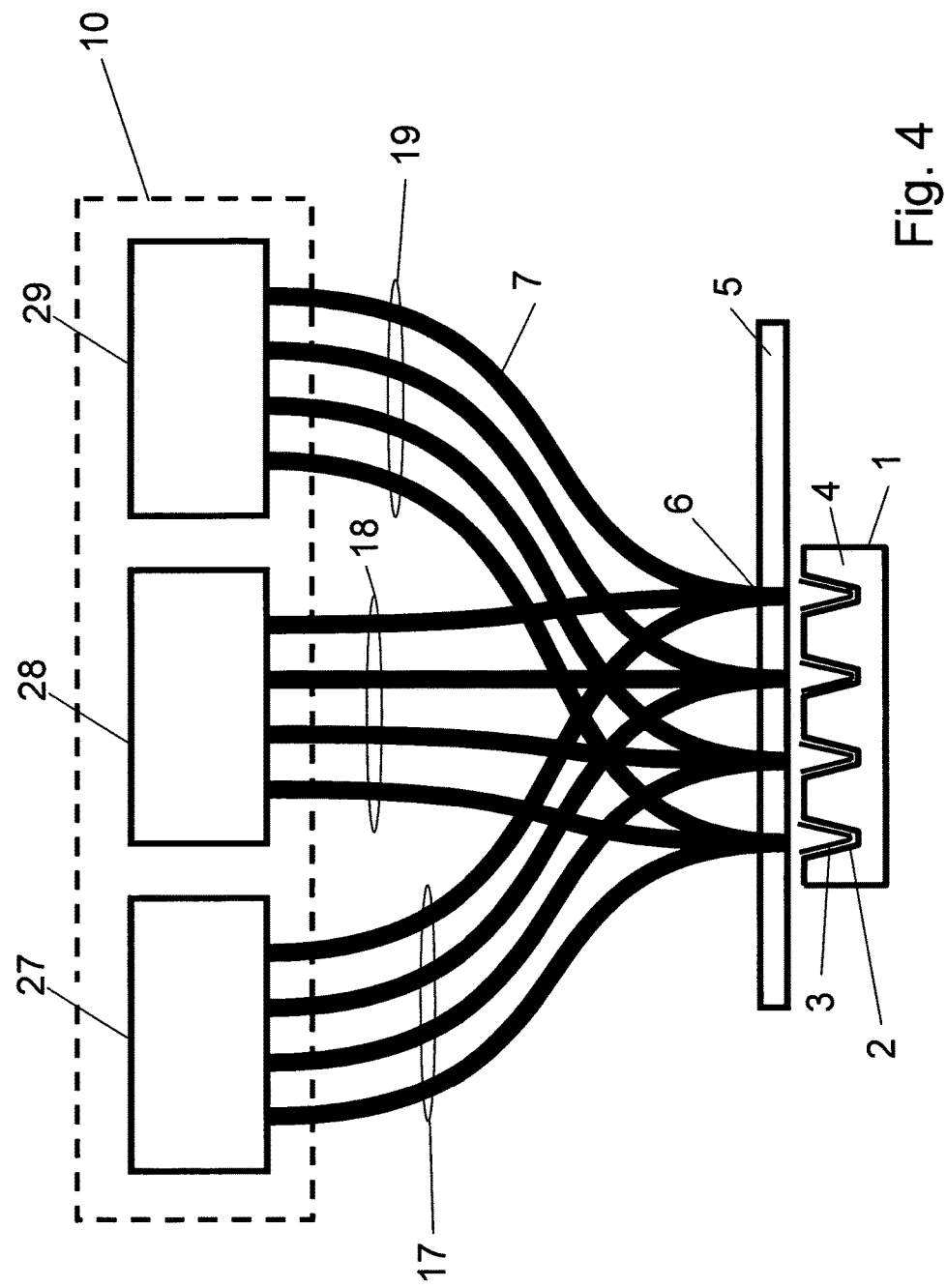
FIG. 4 shows a schematic diagram of a fourth embodiment of an optical system for detecting light in a PCR system.

The embodiments of FIGS. 3 and 4 similarly mask the reaction vessels 3 using a masking plate 5 and only allow light to escape from each reaction vessel via a small aperture 6 in the masking plate 5. Again, an optical fibre 7 is mounted in or at the small aperture 6, but this time, there are several (in this case, three) such small apertures 6 provided adjacent each reaction vessel 3, so that there are several optical fibres 7 per reaction vessel 3 guiding the light from each reaction vessel 3 to several separate portions of the detector 10. Here, there are three such optical fibres 7 guiding the light from each reaction vessel 3 to three separate portions of the detector 10. The detector 10 can thus be provided with separate portions for detecting different specific spectra, for example for detecting red, blue and green colours. Thus, no separate light dispersing element is needed.

As shown in FIG. 3, there are three sets 17, 18 and 19 of optical fibres 7, the fibres within each set guiding light from each reaction vessel 3 to different portions 20, 21, and 22 of the detector 10 for detecting red, green and blue specific spectra, respectively. Each respective portion of the detector 10 includes a sensor 23 and a filter 24, 25, and 26. The second ends of the optical fibres of each set 17, 18 and 19 are arranged adjacent the respective filter 24, 25 and 26 so as to filter the light from the second ends of the respective set of fibres so as to limit the light reaching the respective sensor to a specific spectrum or waveband. Thus, in this case, filter 24 is a red filter, filter 25 is a green filter and filter 26 is a blue filter. The sensors 23 may be the same or may be specific to the colour of light to be sensed by them.

Of course, if the sensors 23 are colour specific, so that they will only detect a specific spectrum, then the filters are not needed, as shown in FIG. 4, and the second ends of each set of optical fibres can be positioned directly adjacent the appropriate one of the sensors, such as red sensor 27, green sensor 28 and blue sensor 29.

Figure 7:
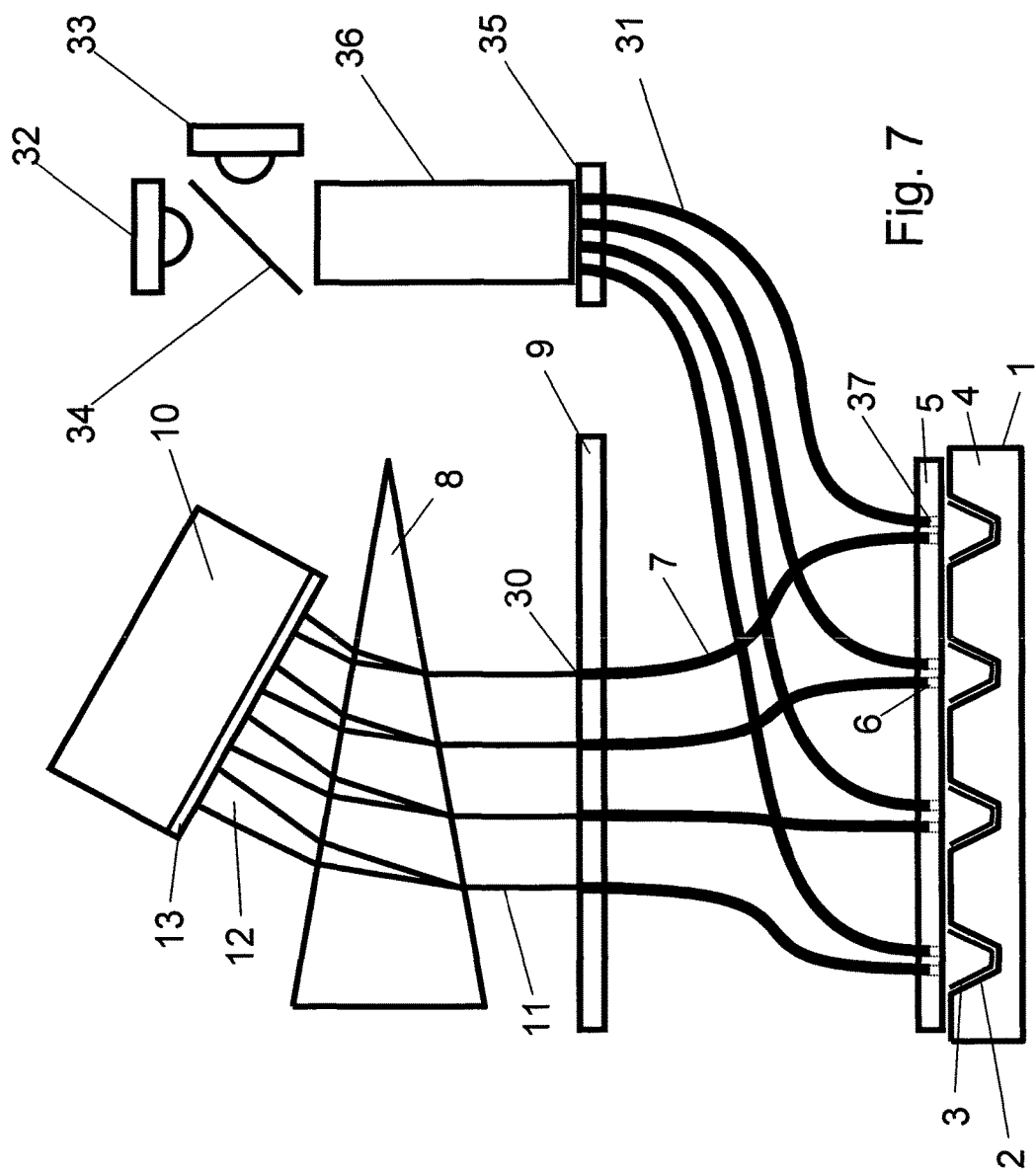
FIG. 7 shows a schematic diagram, similar to FIG. 1, but including excitation in the optical system.

With most of the above described embodiments, it will be appreciated that another small aperture 37 can be position in the masking plate 5 adjacent each reaction vessel 3 with one end of an optical fibre 31 mounted in or at the small aperture 37, as shown in FIG. 7. These optical fibres 31 can be used to bring excitation light to the reaction vessels by having their other ends positioned adjacent one or more sources of excitation light 32, 33. The excitation fibres 31 can be joined together at the excitation accepting end, to make it easier to direct light into them. This may be a drilled plate 35, but this is not necessary, since it is often easier just to bundle the fibres up into an approximately hexagonally packed bundle.

In this embodiment (which is based on the first embodiment described above), one excitation light source may be a blue high intensity LED 32, having an aspire lens thereon. The other excitation light source may be a green LED 33. The LEDs 32 and 33 are arranged on either side of a dichroic mirror 34 so as to combine the excitation light from both LEDs 32 and 33 and to direct it to a homogeniser 36 (essentially a hexagonal prism or cylinder of glass). The dichroic mirror 34 allows blue light from 32 to transmit, and reflects green light from LED 33 into the homogeniser, which to gives more uniform illumination of each excitation lightguide, by reflecting the excitation light multiple times within the homogeniser. This combination produces a spatially homogenous illumination of the polished end of the bundle of excitation fibres, so that each reaction vessel 3 receives fairly equal excitation. It should be noted that the dichroic mirror 34 could be replaced by some other means of directing light from both LEDs into the fibres, for example, a Y shaped lightguide, or even just by having the LEDs angled to both shine at an angle into the fibres.

One embodiment may have 16 pairs of emission/excitation fibres, mounted in cylindrical metal ferrules with one excitation and one emission per ferrule. The ferrules can then be placed in the holes of a conventional heated lid for use. The fibres are made from heat resistant plastics to tolerate contact with the heated lid at ~110C.

Of course, if the tapered fibres are used, that cover substantially the whole of the areas of the top of the reaction vessels, then there would be no room for a further excitation fibre. In this case, the excitation light can be guided by the same fibre that guides the emitted light.

In order, then, to detect the spectra from the reaction vessels, the excitation source (blue or green) is turned on, left to settle for a short time, and an acquisition is then made of an image of the fibre ends. Various correction processes can be applied to this image; for example, correcting for any offset in the reading by subtracting a "dark" image from the acquired image. This dark image is taken with the sensor exposed to as little light as possible, to measure the constant offset that each pixel gives even without light (this is a standard optical correction technique). A further processing stage is to discard pixels of the image which are considered not to be providing a reliable measure of light; for example, so-called hot pixels which give a higher reading due to current leakage or other manufacturing flaws.

The final corrected image then shows the spectra very much as depicted in FIG. 6. To correct for inevitable differences in the positioning of the optics and fibres, a calibration may be performed. This should be necessary only when the instrument has been first manufactured, or after it has been disturbed—due to physical shock, disassembly, etc. Calibration may just use an empty vessel array to reflect the excitation light back into each fibre. The relatively well defined image of the fibre ends in the image can then be seen, since the excitation light has a narrow waveband. The location of each bright point for the reaction vessels can then be found either manually or automatically, and this can be used as a fixed reference point in the spectrum for that reaction vessel. A rectangular (or other shaped) region for the spectrum of each vessel is then defined and stored together with the calibration.

Finally, to interpret a given image, a spectrum is extracted for each vessel. The spectral region for that vessel is looked up from the calibration, and spectral area is then simply scanned along from left to right, averaging the intensity of the pixels in each area to give an intensity for the spectrum itself in the waveband corresponding to those pixels. There are various means of converting, but a simple and adequate way is to average all the pixels in each vertical column of the spectral region, giving more weight to the brighter pixels in the center of the spectrum vertically. Each column average then becomes the intensity for that column, or channel of the reading. A final stage of correction would be to map the channels to the actual wavelength dispersed to that column of the image—this can be done by modelling the dispersing behaviour of the prism or measuring known spectra, but may not always be necessary, since it is possible to compare spectra by channels rather than by wavelength.

Although in the above description, the light emanating from the reaction vessels has been shown as being emitted from an area at the top of the reaction vessel, it will, of course, be apparent that the emitting area can be in any position. The "top" of the reaction vessel is intended to cover any position of the emitting area on the reaction vessel from which the light emanates. Thus, for example, FIG. 8 shows the same system as FIG. 1, with the same elements having the same reference numbers as in FIG. 1, but in a reversed configuration, where the masking plate 5 is positioned adjacent the heater block 4, which, in this case, has holes 38 in the wells 2 between the main elements 39 of the heater block 4 exposing the reaction vessels 3. The reaction vessels 3 are formed in a generally tapered configuration so that the emitting areas of the reaction vessels 3 are at a lowermost point of the tapered reaction vessel. Of course, when the reaction vessels are sealed, the array of reaction vessels in the heater block 4 can be arranged in any desired configuration, so the lowermost point of the tapered reaction vessel 3 as shown in FIG. 8 may well be the "top" in the physical sense.

FIG. 9 shows the same system configuration as FIG. 8, but with the excitation fibres 31 as in the system described above with respect to FIG. 7. In this case, as in FIG. 7, the masking plate 5 is provided with a second aperture 37 adjacent the hole 38 in the bottom of each well 2. As described above, the excitation fibres 31 guide excitation light from excitation light sources 32, 33 to the reaction vessels 2 to excite any fluorophores therein.

FIGS. 10 and 11 illustrate similar embodiments to those of FIGS. 8 and 9, but where the masking plate 5 is formed by the heater block 4 itself. As can be seen, in this case, the heater block elements 39 extend substantially below the wells 2 and provide the apertures 38 into which the fibres 7 (and 31 in the case of FIG. 11) are inserted. In the embodiment of FIG. 11, the fibres 7 and 31 are illustrated as combining into one fibre before they are inserted into apertures 38. The fibres 7 and 31 can be combined in any known way, for example by a form of parallel combination, for example with multiple fibres being contained in the same outer jacket.

Turning now to FIG. 12, there is shown there an arrangement using an array of capillary tubes 40 mounted in a mounting plate 41 in place of the reaction vessels 2. The capillary tubes 40 may be heated, for example, by blowing heated gas around them. In this case, the remaining features are similar to those of FIG. 10 and have the same reference numerals, except that the ends of the fibres 7 protrude through the masking plate 5 to enable them to be positioned appropriately closely to the end of the respective capillary tube 40. As best shown in FIG. 16, because a fibre 7 has a limited angle of reception 42 (or emission), by having the end of the fibre relatively close to the reaction fluid 43 in the capillary means that any tolerances in the position of the capillary, which may be somewhat greater in the case of the hanging capillary tubes 40 than in wells in a heater block, are allowed for. Of course, if the end of the fibre is too close, where the capillary end will only just fit into the intersection of the excitation and emission "cones", any horizontal movement of the capillary results in light not being captured. On the other hand, if the fibres are further away, such as in the mounting plate 5, then variations in position, or movement of the capillary tubes 40 when in position, for example due to the pressure of the heating gas, would be allowed for due to the increase in the cone of reception 42, but there is a corresponding reduction in the efficiency of light collection and in excitation due to the increase in size of the excitation cone. As shown in the embodiment of FIG. 12, Light Emitting Diodes (LEDs) 44 of appropriate excitation light may be provided adjacent each capillary tube 40. In the alternative embodiment shown in FIG. 13, the excitation light is provided in the same manner as in previous embodiments with excitation fibres 31 being used to bring excitation light to the capillary tubes 40 from one or more sources of excitation light 32, 33.

FIG. 14 shows a still further embodiment, similar to that of FIG. 10, where the same elements have the same reference numerals. In this case, the excitation light is provided by LEDs 44, as in the embodiment of FIG. 12. However, the holes 38 in the heater block 4 through which the ends of the fibres 7 extend, are here positioned to extend upwardly from the base of the heater block and then to extend to the wells 2 in the heater block from a side thereof, so that the ends of the fibres 7 are adjacent the sides of the reaction vessels 3. It will, of course, be appreciated that the drawing does not show the full extent of the holes 38, but only shows the fibres 7 extending upwardly through the heater block 4 in a schematic manner, with the hole 38 being shown adjacent the side of the well 2. The fibres 7 are also shown with a sharp right angle although, in practice, they would, of course, not be so sharply angled. As best shown in FIGS. 17 and 18, the fibres 7 need to be accurately positioned adjacent the side of the reaction vessel 3 so that the angle of reception 42 can capture as much light as possible emanating from the reaction fluid 43. However, as explained above, once in position, the reaction vessels 3 will not move unduly, so the results will not be affected as much as with the capillary tubes 40.

FIG. 15 shows a further embodiment, similar to that of FIG. 14, in which the same elements have the same reference numerals. In this case, the holes 38 are made relatively small, with the ends of the fibres being mounted within the holes so that the side of the well 2 in the heating block element 39 forms the masking plate to prevent light other than that passing through the aperture 38 from reaching the fibre 7. Although not shown in FIG. 15, it will be appreciated that the excitation light could be provided by an excitation fibre 31 guiding excitation light from one or more sources of excitation light, as in previous embodiments. Although the excitation fibre could be provided in the same hole 38 as the emission fibre 7, as shown in FIG. 17, this would mean that neither the excitation fibre 31 nor the emission fibre 7 would be in the ideal position for the reaction vessel, since both the angle of reception 42 and the angle of emission 45 would be off-centre. FIGS. 19 and 20 show how the two fibres could be separated within the heater block so that their ends are adjacent the reaction vessel separated by 90° so as to minimize the amount of excitation light that might enter the emission fibre 7. As can be seen in FIG. 19, both the angle of reception 42 and the angle of emission 45 are now centred on the reaction vessel 3, with reaction fluid 43 being wholly within the angles of reception and emission of the respective fibres.

It will be appreciated that although only a few particular embodiments of the invention have been described in detail, various modifications and improvements can be made by a person skilled in the art without departing from the scope of the present invention. For example, it will probably often be useful to have more optical components in the path from plate 9 to plane 13 in FIG. 1. For example, it might be useful to "fold" the optical path 11 by adding one or more mirrors. This reduces the size of the entire optical assembly, whilst making very little difference the actual operation or performance of the system. Another example of an additional component is to have one or more additional lenses before or after the prism 8 to provide additional correction of the light path—again this may not be essential, but is a well known optical technique to correct for various aberrations, etc. Such additional optical elements may form part of the dispersing element, but may be separate components.

It will also be appreciated that, although the image plane 13 in FIG. 1 is shown at the front of the detector 10, it could, alternatively, be towards the back of the detector, if the detector consists of a CMOS sensor with a suitable camera lens module in front of it. In the embodiments shown in FIGS. 14 and 15, the fibres pass vertically through the block 4, however, it will be appreciated that, in some circumstances, the vertical portion of the fibres could be arranged to be outside the block—for example in a block having one row of wells, the fibres could simply pass horizontally from the "side face" of the block to the wells, since there are no other wells in the way. A mount with two rows of wells could obviously be arranged the same way, with fibres entering from the two longer vertical sides of the mount.

The invention claimed is:

1. Apparatus for detecting light, the apparatus comprising:
a plurality of reaction vessels, each of the reaction vessels being mounted to a heater block of a thermal cycler, each of the reaction vessels comprising a receptacle portion therein having an interior volume in which a chemical or biochemical reaction may occur and within which volume the light may be produced, each of the reaction vessels having an emitting area through which at least part of the light produced within the interior volumes of the reaction vessels passes to emanate from the reaction vessels, wherein the heater block is controlled to thermally cycle the interior volumes of the reaction vessels;
a masking element having an array of apertures arranged so that there is at least one aperture adjacent each of the emitting areas of the reaction vessels and at least a part of the light produced in the interior volumes of the receptacle portions of the reaction vessels passes therethrough, at least one of the apertures being smaller than the emitting area of the corresponding reaction vessel;
a light detecting device comprising at least one detector and controlling electronics programmed to control the at least one detector so that at least part of the light that is produced in the interior volumes of the receptacle portions of all of the reaction vessels in which light is produced is detected by the light detecting device; and
a plurality of light waveguides comprising at least one light waveguide for each reaction vessel, each of the light waveguides arranged to guide at least a part of the light from a respective aperture of the array of apertures in the masking element to the light detecting device, the light waveguides having first ends mounted to or in at least one of the respective apertures in the masking element, which respective apertures have a size similar to that of the first ends of the respective light waveguides, wherein the controlling electronics of the light detecting device are programmed to control the at least one detector so that the light received from each of the reaction vessels in which light is produced is detected simultaneously by the light detecting device.

2. Apparatus according to claim 1, further comprising a light dispersing device for dispersing the light that escapes from the small apertures in the masking element into a dispersed spectrum.

3. Apparatus according to claim 2, further comprising a plurality of light waveguides arranged to guide light from the small apertures in the masking element to the light dispersing device.

4. Apparatus according to claim 3 wherein the light detecting device comprises a plane onto which the dispersed spectra of light from the apertures is produced, and the at least one detector detects specific spectra within the dispersed spectra.

5. Apparatus according to claim 3, wherein the light dispersing device comprises a light splitting device for dispersing the light into different wavebands.

6. Apparatus according to claim 1, wherein the masking element comprises at least two of the apertures associated with each of the reaction vessels, each of the plurality of light waveguides being arranged to guide light from a respective aperture to the light detecting device, wherein one light waveguide associated with each of the reaction vessels guides the light to one portion of the light detecting device for detecting one specific spectrum of the light and another light waveguide associated with each of the reaction vessels guides the light to another portion of the light detecting device for detecting one specific spectrum of the light.

7. Apparatus according to claim 1, further comprising a further light waveguide for each of the reaction vessels arranged between a further aperture in the masking element adjacent each of the reaction vessels and an excitation light source for guiding excitation light from the excitation light source to each of the reaction vessels.

8. Apparatus according to claim 1, further comprising one or more additional light waveguides arranged to guide light from one or more excitation light sources to the light detecting device.

9. Apparatus according to claim 1, wherein the emitting area is provided in a wall of each of the reaction vessels and the masking element is formed by the heater block of the thermal cycler.

10. Apparatus according to claim 1, wherein the emitting area is provided in a bottom of each of the reaction vessels and the masking element is formed by the heater block of the thermal cycler.

11. Apparatus for detecting light, said apparatus comprising:
a plurality of reaction vessels, each of the reaction vessels being mounted to a heater block of a thermal cycler, each of the reaction vessels comprising a receptacle portion therein having an interior volume which contains a chemical or biochemical reaction of at least one reagent therein and within which interior volume the light is produced and emanates, and each reaction vessel having an emitting area through which at least part of the light produced within the interior volume of the reaction vessel thereof passes to emanate from the receptacle portion thereof, wherein the chemical or biochemical reaction of the reagent within the receptacle portion of at least a first reaction vessel of the reaction vessels may produce light that can emanate through the emitting area of the first reaction vessel, wherein the heater block is controlled to thermally cycle the interior volumes of the reaction vessels;
a masking element having an aperture adjacent each of the reaction vessels, the apertures being arranged so that at least a part of the light produced in the interior volumes of the receptacle portions of the reaction vessels passes simultaneously through the apertures;
a light dispersing device and a plurality of light waveguides arranged to guide at least part of the light from the apertures in the masking element to the light dispersing device for dispersing the light from each of the light waveguides into a dispersed spectrum, the light waveguides having first ends mounted to or in a respective aperture in the masking element, which respective apertures have a size similar to that of the first ends of the respective light waveguides; and a light detecting device comprising at least one detector and controlling electronics programmed to control the at least one detector, the light detecting device being arranged to receive the dispersed spectra and the controlling electronics of the light detecting device being programmed to control the at least one detector so that the light detecting device simultaneously detects specific spectra of light within the dispersed spectra.

12. Apparatus according to claim 11, further comprising an output array element having a plurality of output apertures arranged in a predetermined array adjacent the light dispersing device, wherein each of the light waveguides comprises a first end constrained to receive light from a respective one of the apertures in the masking element and a second end constrained at a respective one of the apertures of the output array element to direct light to the light dispersing device.

13. Apparatus according to claim 11, wherein each of the apertures in the masking element have a size smaller than the emitting area of the receptacle portion of the reaction vessel thereof, and the light waveguides are arranged to capture at least a part of the light from the apertures in the masking element, the apparatus further comprising a further light waveguide for each of the reaction vessels arranged between a further aperture in the masking element adjacent each of the reaction vessels and an excitation light source for guiding excitation light from the excitation light source to the reagent within the receptacle portion of the first reaction vessel of the reaction vessels.

14. Apparatus according to claim 12, wherein each of the apertures in the masking element has a size similar to the emitting area of the receptacle portion of the reaction vessel thereof, and each of the light waveguides tapers in diameter from their first end thereof, which has a diameter similar to a respective one of the apertures in the masking element, and the second end of each of the light waveguides is smaller in diameter than the first end thereof.

15. Apparatus according to claim 12, wherein the light detecting device comprises a plane onto which the dispersed spectrum from the dispersing element is produced, and the at least one detector detects specific spectra within the dispersed spectra, and the array of the output apertures in the output array element is arranged so that the dispersed spectra on the plane of the light detecting device do not overlap, at least within the spectral range where there is light emitted from the reaction vessels and passed to the light detecting device.

16. Apparatus according to claim 15, wherein the array of output apertures in the output array element has a smaller area than the array of apertures in the masking element.

17. Apparatus according to claim 11, further comprising a plurality of excitation light sources, which provide excitation light of the same or different spectra, the excitation light from each of the excitation light sources being guided to each of the reaction vessels.

18. Apparatus according to claim 11, further comprising one or more additional light waveguides arranged to guide excitation light from one or more excitation light sources to the light detecting device.

19. Apparatus according to claim 11, wherein the emitting area is provided in a wall of each of the reaction vessels and the masking element is formed by the heater block of the thermal cycler.

20. Apparatus according to claim 11, wherein the emitting area is provided in a bottom of each of the reaction vessels and the masking element is formed by the heater block of the thermal cycler.

21. Apparatus for detecting spectra in light emanating from a plurality of reaction vessels of an array of reaction vessels, each of the reaction vessels being mounted to a heater block of a thermal cycler, each of the reaction vessels comprising a receptacle portion therein in which a reagent is contained and a chemical or biochemical reaction is occurring and from which light is emanating from within the receptacle portion, each of the reaction vessels having an emitting area through which the light emanating from within the receptacle portion thereof emanates from the receptacle portion thereof, wherein at least a part of the light emanating from within the receptacle portions of the reaction vessels passes through the emitting areas of the reaction vessels, wherein the heater block is controlled to thermally cycle the interior volumes of the reaction vessels, the apparatus comprising a plurality of light waveguides comprising at least one light waveguide associated with each of the reaction vessels, the light waveguides being arranged to guide at least part of the light from the emitting areas of the reaction vessels to a light dispersing device for dispersing the light from each of the light waveguides into a dispersed spectrum of light, a light detecting device comprising at least one detector and controlling electronics programmed to control the at least one detector so that the light detecting device simultaneously detects specific spectra in the dispersed spectra of light and at least one excitation arrangement for providing excitation light to the reagent within the receptacle portion of each of the reaction vessels.

22. Apparatus according to claim 21, wherein the excitation arrangement comprises an excitation light source and a second light waveguide associated with each of the reaction vessels for guiding excitation light from the excitation light source to the receptacle portion of each reaction vessel.

23. Apparatus according to claim 21, wherein the excitation arrangement comprises an excitation light source arranged in or adjacent the receptacle portion of each of the reaction vessels.

24. Apparatus according to claim 21, wherein the emitting area is provided in a wall of each of the reaction vessels and the masking element is formed by the heater block of the thermal cycler.

25. Apparatus according to claim 21, wherein the emitting area is provided in a bottom of each of the reaction vessels and the masking element is formed by the heater block of the thermal cycler.

* * * * *